United States Patent
Blankenship

Patent Number: 6,165,495
Date of Patent: Dec. 26, 2000

[54] DRUG DELIVERY SYSTEM

[76] Inventor: Mildred Blankenship, 14814 Rutherford, Detroit, Mich. 48227

[21] Appl. No.: 08/732,221

[22] PCT Filed: Apr. 29, 1994

[86] PCT No.: PCT/US94/04730

§ 371 Date: Oct. 25, 1996

§ 102(e) Date: Oct. 25, 1996

[87] PCT Pub. No.: WO94/25011

PCT Pub. Date: Nov. 10, 1994

[51] Int. Cl.$^7$ ................ A61K 9/68; A61K 9/62; A61K 9/36; A61K 9/16

[52] U.S. Cl. .................. 424/440; 424/461; 424/479; 424/493

[58] Field of Search .................. 424/440, 441, 424/439, 418, 459, 461, 479, 481, 493, 496, 499, 500, 464

[56] References Cited

U.S. PATENT DOCUMENTS

| | | | |
|---|---|---|---|
| 109,677 | 11/1870 | Seitz | 424/50 |
| 122,507 | 1/1872 | Wills | 424/50 |
| 352,466 | 11/1886 | Huttemeyer | 424/50 |
| 1,991,139 | 2/1935 | Clark | 424/50 |
| 2,311,923 | 2/1943 | Lautmann | 424/50 |
| 4,229,482 | 10/1980 | Kreske, Jr. | 426/134 |
| 4,246,256 | 1/1981 | Lembke et al. | 424/50 |
| 4,255,414 | 3/1981 | Lembke et al. | 424/50 |
| 4,271,142 | 6/1981 | Puglia et al. | 424/14 |
| 4,551,329 | 11/1985 | Harris et al. | 424/22 |
| 4,671,953 | 6/1987 | Stanley et al. | 424/440 |
| 4,749,575 | 6/1988 | Rotman | 424/441 |
| 4,847,090 | 7/1989 | Della Posta et al. | 424/440 |
| 4,857,333 | 8/1989 | Harold | 424/442 |
| 4,863,737 | 9/1989 | Stanley et al. | 424/440 |
| 4,885,173 | 12/1989 | Stanley et al. | 424/440 |
| 4,929,508 | 5/1990 | Sharma et al. | 424/439 |
| 4,933,183 | 6/1990 | Sharma et al. | 424/439 |
| 5,028,411 | 7/1991 | Callingham et al. | 424/45 |
| 5,059,416 | 10/1991 | Cherukuri et al. | 424/48 |
| 5,085,634 | 2/1992 | Lackney | 604/77 |
| 5,102,664 | 4/1992 | Day | 424/440 |
| 5,162,037 | 11/1992 | Whitson-Fischman | 600/12 |
| 5,484,602 | 1/1996 | Stanley et al. | 424/440 |

Primary Examiner—Bradley L. Sisson
Attorney, Agent, or Firm—Kohn & Associates

[57] ABSTRACT

A drug delivery system comprising a dissolvable solid portion (10) having an outer (12) and inner surface (14) and a cavity (16) for receiving fluid. The cavity (16) is surrounded by, and contained within, the solid portion (10). Both the solid portion (10) and the cavity (16) are supported by a handle (20). A method of administering a drug is also disclosed.

9 Claims, 1 Drawing Sheet

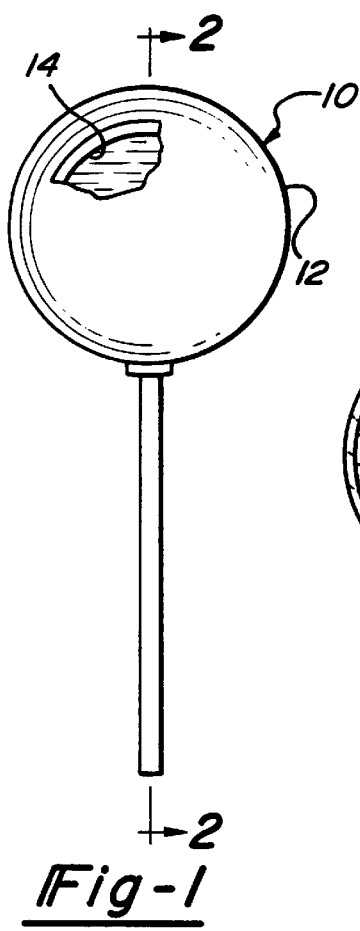
Fig-1
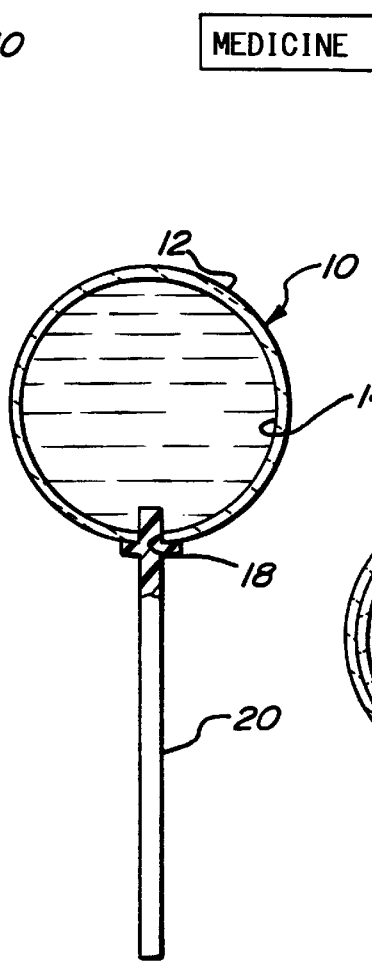
Fig-2
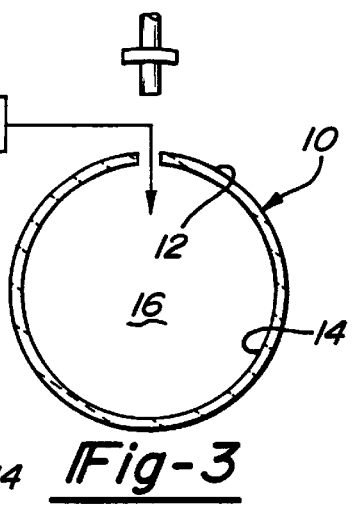
Fig-3
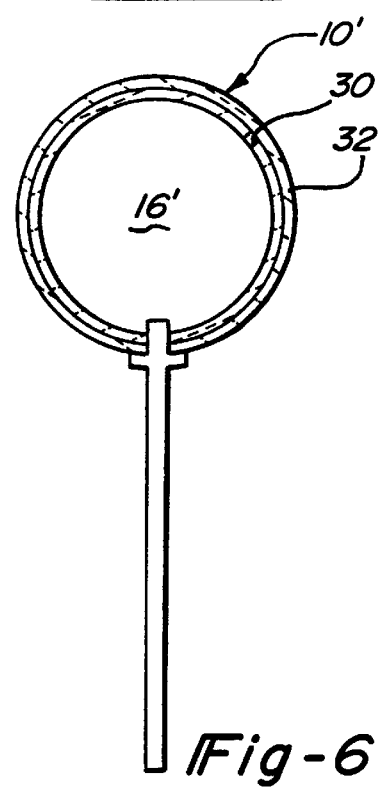
Fig-6
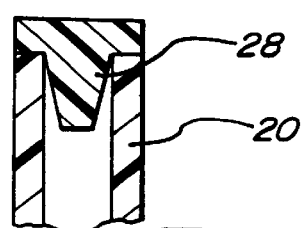
Fig-4
Fig-5 ns. More particularity, the
present invention relates to a drug delivery system that will
be administered to and accepted by children more readily.

DRUG DELIVERY SYSTEM

TECHNICAL FIELD

This invention relates to a drug delivery system and a method for administering the same. More particularity, the present invention relates to a drug delivery system that will be administered to and accepted by children more readily.

BACKGROUND OF THE INVENTION

Oral administration of medicaments to children presents special problems. Children often have difficulty swallowing pills and due to the undesirable taste of liquid medicaments may refuse to swallow the same.

Pills, capsules and tablets are generally not acceptable for use in small children because if improperly swallowed, they may lodge in the child's throat thereby causing choking. This problem may be overcome by grinding of the pill or tablet into a powder which facilitates administration. However, the grinding, collecting and administering process often results in a loss of varying portions of the medicament and may effect drug absorption and thereby effecting dosage accuracy.

As previously stated, the poor taste often associated with liquid medicaments creates problems in administering these medicaments to children. Further, children often are frightened of taking even liquid medicaments and actively resist ingesting the same. These situations may lead to aspiration of the liquid medicament by the child. Choking is therefore a problem, even with liquid medicaments.

As shown in U.S. Pat. No. 2,311,923 to Lautmann issued on Feb. 23, 1943 and U.S. Pat. No. 4,271,142 to Puglia issued Jun. 2, 1981, medicaments may be placed in candy form to facilitate their administration, particularly to children. Lautmann '923 teaches a cough drop having a hard, edible, candy shell and a medicated liquid center. While the cough drop overcomes the problems associated with liquid medicaments, other problems arise in administrating this type of solid candy medicament to a child. Of particular concern is that this form of medicament may be accidently swallowed and lodge in a child's throat resulting in choking. This drawback is associated with the medicaments of both the Lautmann '923 and Puglia '142 type candy medicaments.

The present invention overcomes the problems associated with a candy coated medicament by providing a handle for support. The handle also may be used as sealing means to seal the liquid medicament in the cavity provided by the dissolvable candy shell.

The prior art with respect to handle supported medicaments, such as U.S. Pat. Nos. 4,671,953 and 4,863,737 both to Stanley, issued on Jun. 9, 1987 and Sep. 5, 1989 respectively, generally teach medicated lollipops wherein the medicament is dispersed throughout the entire confectionery matrix of the lollipop. The medicament enters the patient's system through a transmucosal dosage. Although the Stanley patents recognize the utility of medicated lollipops in controlling the dosage provided to the patient, the dosage is varied by placing the medicament in different concentrations in the various solid layers of the lollipop. This requires monitoring of the patient to ensure administration of the proper dosage. According to the prior Stanley patents, once the desired analgesic effect is obtained, the lollipop is taken away from the patient. Hence, active supervision is necessary to regulate the dosage.

One problem associated with the administration of medicaments in the manner disclosed in the prior Stanley patents is that accidental ingestion of the entire lollipop or a significant portion thereof may result in over medication of the patient. Such accidental ingestion may occur by chewing the medicament rather than allowing it to dissolve slowly in the patient's mouth. Further, the Stanley patents, as well as other prior handle supported medicaments such as U.S. Pat. No. 5,085,634 issued to Lackney on Feb. 4, 1992 and U.S. Pat. No. 4,551,329 issued to Harris on Nov. 5, 1984, do not teach nor do they suggest the use of liquid medicaments or the dispensing of medicaments by a pharmacist into a specially adapted candy shell having a cavity for receiving fluid medicaments.

In general, the present invention provides a drug delivery system which allows easy administration to children without the problems of the prior art discussed above.

SUMMARY OF THE INVENTION

The present invention relates to a drug delivery system and a method for administering the same. The drug delivery system consists of a dissolvable solid portion having an outer and inner surface. A cavity surrounded by and contained within the solid portion is provided for receiving fluid. A passageway may be provided extending through the inner and outer surface of the solid portion into the cavity. Both the solid portion and the cavity are supported by a handle.

In use, a fluid medicament is injected through a passageway into the cavity that is surrounded by and contained within dissolvable shell. The cavity is filled with a fluid medicament and the passageway is sealed with an elongated member.

FIGURES IN THE DRAWINGS

FIG. 1 is a cut away plan view of one embodiment of the drug delivery system;

FIG. 2 is a cross section of the drug delivery system taken along 2—2 of FIG. 1;

FIG. 3 is a partial cross-section of the drug delivery system of FIG. 1 wherein the handle is shown removed so as to allow the injection of a medicament into the cavity;

FIG. 4 is a partial cross-section of the handle and sealing area of the drug delivery system;

FIG. 5 is a cross-section of the end portion of the handle of the drug delivery system; and FIG. 6 is a cross-sectional view of a second embodiment of the invention.

DETAILED DESCRIPTION OF THE INVENTION

The present invention relates to a drug delivery system and the method for delivering the same.

The drug delivery system of the present invention is designed so that it may be administered to, and accepted more readily by, children. It generally consists of a dissolvable solid portion 10 having an outer 12 and an inner 14 surface. The inner surface 14 of the solid portion 10 defines a cavity 16 for receiving fluid. This cavity 16 is surrounded by and contained within the solid portion 10. A passageway 18 may extend through the outer 12 and inner surfaces 14 of the solid portion 10 into the cavity 16.

The solid portion 10 and the cavity 16 are supported by a handle 20. In one embodiment, the handle 20 may be hollow or solid and may be used to seal the passageway 18 through the dissolvable solid portion 10. In another embodiment, the handle 20 may be embedded into the solid portion 10 or attached thereto with confectioner's glue.

The dissolvable solid portion 10 comprises a candy shell. The use of candy makes the drug particularly appealing to small children. The candy may contain conventional sweeteners such as sugar, corn syrup and the like; or an artificial sweetener may be used. Of course, a variety of flavorings may be used as in well known in candy preparations. The dissolvable candy shell may be of any shape. In the instance of administration to small children, animal shapes may be used for the solid portion 10.

A cavity 16 is provided for receiving fluid medicaments in the center of the drug delivery system. The fluid center is intended to include medicaments in the form of liquids, gels, cream and any other non-solid that does not react with the candy shell.

The handle 20 of the drug delivery system is an elongated member which allows gripping by the patient, generally a child. The handle 20 may also be a safety loop paper or twine handle. The handle 20 may be affixed to the candy shell with confectioner's glue or it may be embedded into the candy shell during manufacturing. In yet another embodiment, the handle 20 is formed of a hollow outer portion 22 which extends through the passageway 18 of the solid outer portion 10 into the cavity 16. An elongated inner handle portion (not shown) is provided for sealing the hollow outer portion 22. Alternatively, the handle 20 may be separate so that it may serve as the sealing means for the passageway 18 which is provided in and extends through the outer shell 10 into the cavity 16. In yet another embodiment, the handle is hollow and extends though the passageway 18. The handle 20 is provided with a one way valve 26 which allows fluid to be injected into the cavity 16 through the passageway 18, but which valve 26 prevents fluid medicaments from flowing in the opposite direction. The end of the handle 20 is sealed with a plug or other stopper member 28 as shown in FIG. 5.

A second embodiment of the present drug delivery system shown in FIG. 6. In this embodiment, the solid portion 10' includes a hole 30 extending therethrough for release of drug therefrom when exposed. The system includes a dissolvable layer 32 disposed over the opening 30 for sealing closed the opening. The layer 32 is dissolvable to allow for release of the drug from the cavity 16 through the opening 30. The dissolvable layer can be either disposed over the opening 30 or it can be disposed over the entire outer surface of the shell 10 is an outer coating.

By disposing the layer 32 over the entire shell 10, a drug release indicator can be derived. For example, the outer shell 10 can be one color and the layer 32 can be a second color such that upon dissolution of the outer layer 32, there is an apparent change of color which indicates when the layer 32 is completely dissolved. At the same time, the opening 30 is exposed to release drug therethrough from the inner cavity 16. Thusly, the change of color indicates release of drug from the solid portion 10.

This release indication is significant where a younger child is being given the drug and it may not be desirable for the younger child to chew on the solid portion, especially when choking may be a problem as a result of the chewed fractured coating.

The dissolvable layer can be made from various materials known in the art. For example, the dissolvable layer 32 can be sugar layer or can be made from various membrane materials dissolvable in the oral cavity known in the drug delivery art, such as cellulose acetate, cellulose acetate butyrate and combinations thereof. Of course, the thickness of the dissolvable layer 32 will determine the rate of release of the drug.

The present drug delivery system may be utilized as a kit containing the dissolvable candy shell 10 and the elongated member 20 which may be inserted into the passageway 18 for sealing engagement therewith. In this embodiment, the administration of the drug delivery system may be carried out by a pharmacist at the point of sale by injecting a fluid medicament through the passageway 18 provided in the candy shell 10, filling the cavity 16 that is contained within and surrounded by the candy shell 10 with the fluid medicament and sealing the passageway 18 with the elongated member 20. The elongated member 20 serves as the handle. Alternatively, the kit may contain the dissolvable candy shell 10 having a handle consisting of a hollow outer portion 22 and an elongated inner handle portion which serves as a plug that prevents fluid from flowing out of the cavity 16. In yet another embodiment, the candy shell 10 is affixed to the hollow handle 20 which is provided with a valve 26. In this embodiment, the pharmacist may inject the fluid medicament through the valve 26 in the hollow handle 20 into the cavity 16 with a needle and syringe or other such instrument. A stopper member 28 may be provided to seal the end of the hollow handle. However, in this embodiment, the stopper member is not necessary because the valve 26 prevents fluid medicament from flowing out of the cavity 16. In use, the drug delivery system of this embodiment may also be carried out by a pharmacist at the point of sale, by injecting the medicament through the hollow handle portion into the cavity and sealing the fluid in the cavity by inserting the elongated inner handle portion into the outer portion.

The invention has been described in an illustrative manner, and it is to be understood that the terminology which has been used is intended to be in nature of words of description rather than of limitation.

Obviously, many modifications and variations of the present invention are possible in light of the above-teachings. It is, therefore, to be understood that within the scope of the appended claims, wherein reference numerals are merely for convenience and are not intended to be in any way limiting, the invention may be practiced otherwise than as specifically described.

REFERENCES CITED

1. U.S. Pat. No. 2,311,923 (Lautmann)
2. U.S. Pat. No. 4,271,142 (Puglia)
3. U.S. Pat. No. 4,671,953 (Stanley)
4. U.S. Pat. No. 4,863,737 (Stanley)
5. U.S. Pat. No. 5,085,634 (Lackney
6. U.S. Pat. No. 4,551,329 (Harris)

What is claimed is:

1. A drug delivery system comprising a dissolvable candy shell (10) having an outer (12) and inner (14) surface, a cavity (16) for receiving a fluid, an opening extending through said outer (12) and inner (14) surfaces of said candy shell (10) into said cavity (16) thereby forming a passageway (17), sealing means (20) insertable into said passageway (18) for sealing engagement therewith, said sealing means (20) including an elongated hollow member extending from said passageway (18) to serve as a handle (20) wherein the hollow member has attached to the inner surface of the passageway a valve (26) that serves to block reverse flow of the fluid from the chamber.

2. A drug delivery system according to claim 1 wherein said elongated member is affixed to said candy shell portion with confectioner's glue.

3. A drug delivery system according to claim 3, wherein said cavity (16) is filled with fluid containing a medicament.

4. A method of administering a fluid drug into the cavity (16) of the drug delivery system of claim 9 comprising injecting a fluid medicatement through a hollow elongated member (20) past a valve (26) into a cavity (16) surrounded and contained within a candy shell (10) said valve (26) preventing fluid from flowing out of said cavity (16).

5. A method according to claim 4, wherein the elongated member is insertable into the passageway for sealing engagement therewith.

6. A drug delivery system as set forth in claim 1 wherein said solid portion (10') includes a hole extending therethrough for release of drug therefrom when exposed, said system further including a dissolvable layer (32) disposed over said opening (30) for sealing closed said opening and being dissolvable to allow for release of the drug from said cavity (16) through said opening (30).

7. A drug delivery system as set forth in claim 6 wherein said dissolvable layer (32) consists of a sugar cellulose acetate, cellulose acetate butyrate, and combinations thereof.

8. A drug delivery system as set forth in claim 6 wherein said dissolvable layer (32) is dispersed completely over said solid portion (10).

9. A drug delivery system as set forth in claim 8 wherein said dissolvable layer is a different color than said solid layer whereby during use a change in color indicates release of the drug from said solid portion (10).

* * * * *